United States Patent [19]
Hernandez

[11] Patent Number: 5,668,847
[45] Date of Patent: *Sep. 16, 1997

[54] APPARATUS AND METHOD FOR ADJUSTING RADIATION IN A RADIATION-EMITTING DEVICE

[75] Inventor: Francisco M. Hernandez, Concord, Calif.

[73] Assignee: Siemens Medical Systems, Inc., Iselin, N.J.

[*] Notice: The term of this patent shall not extend beyond the expiration date of Pat. No. 5,563,925.

[21] Appl. No.: 665,153

[22] Filed: Jun. 13, 1996

Related U.S. Application Data

[63] Continuation of Ser. No. 504,937, Jul. 20, 1995, Pat. No. 5,563,925.

[51] Int. Cl.⁶ ............................................. G21F 5/04
[52] U.S. Cl. ...................... 378/65; 378/150; 250/492.1
[58] Field of Search ........................ 378/65, 108, 145, 378/147, 156, 151, 152, 159, 150; 250/492.1, 492.3, 505.1

[56] References Cited

U.S. PATENT DOCUMENTS 5,148,032  9/1992  Hernandez ........................ 250/492.1
5,563,925  10/1996  Hernandez ........................ 378/150

OTHER PUBLICATIONS

Faiz M. Khan, Ph.D., "The Physics of Radiation Therapy", 2d ed., pp. 200–206 no date.

Siemens Product Brochure, "Digital Systems for Radiation Oncology", pp. 1–16 no date.

Primary Examiner—David P. Porta
Attorney, Agent, or Firm—Heather S. Vance

[57] ABSTRACT

In a radiation emitting device, particularly in a radiation treatment device, the actual radiation delivered to an object via a radiation beam is adjusted dependent on the dimensions of an opening in a plate arrangement provided between a radiation source and an object so that the radiation output has a constant wedge factor over an irradiation field, regardless of the size of the opening. The wedge factor is defined as the ratio between a reference radiation output along a reference axis of the beam with a predetermined physical wedge in the beam path and an actual radiation output of the beam in a substantiallylossless beam path.

11 Claims, 3 Drawing Sheets

FIG. 3
(PRIOR ART)
FIG. 4
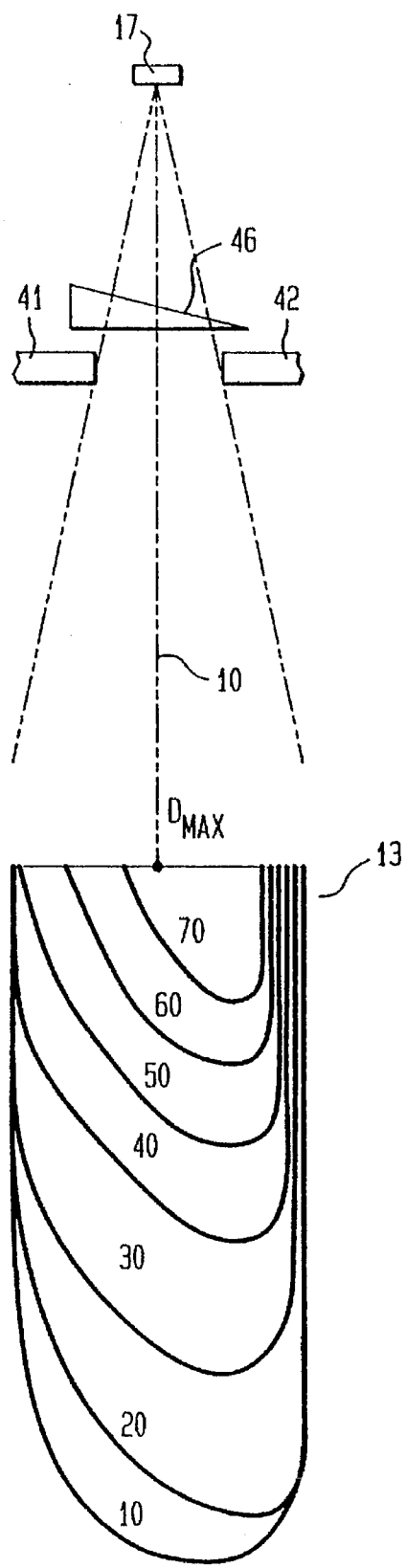
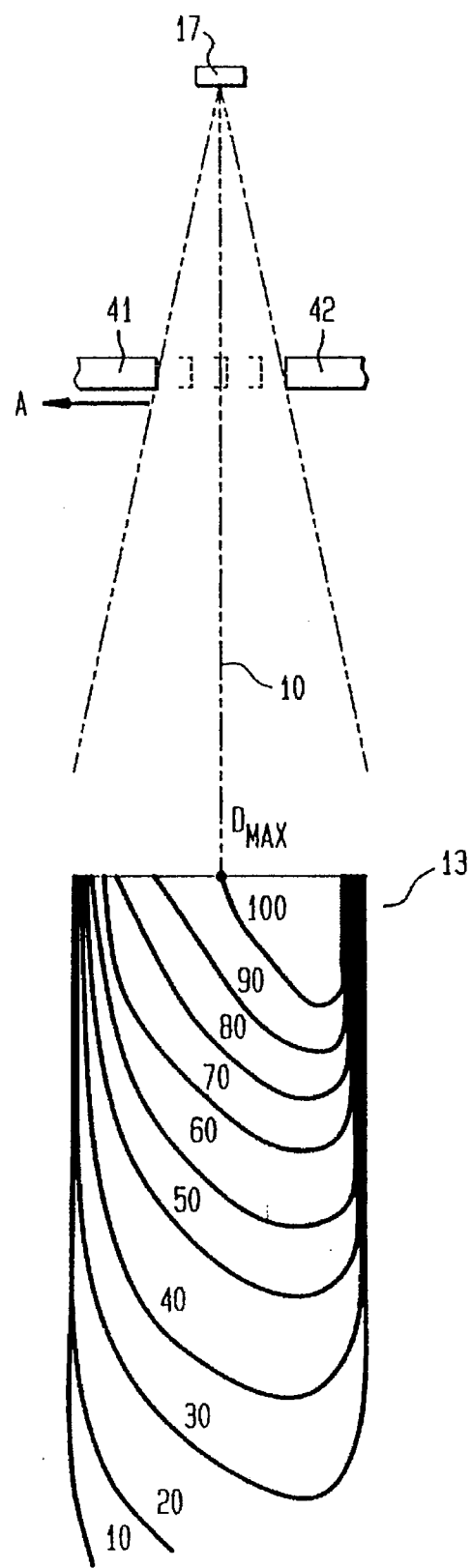

APPARATUS AND METHOD FOR ADJUSTING RADIATION IN A RADIATION-EMITTING DEVICE

This is a continuation, of application Ser. No. 08/504,937 filed Jul. 20, 1995 now U.S. Pat. No. 5,563,925.

BACKGROUND OF THE INVENTION

1. Field of the Invention

The invention relates to a radiation emitting device, and particularly to a system and a method for adjusting the radiation delivered to an object in a radiation treatment device.

2. Description of the Related Art

Radiation-emitting devices are generally known and used, for instance as radiation therapy devices for the treatment of patients. A radiation therapy device generally comprises a gantry which can be swiveled around a horizontal axis of rotation in the course of a therapeutic treatment. A linear accelerator is located in the gantry for generating a high-energy radiation beam for therapy. This high energy radiation beam can be an electron radiation or photon (X-ray) beam. During treatment, this radiation beam is trained on one zone of a patient lying in the isocenter of the gantry rotation.

In order to control the radiation emitted toward an object, a beam-shielding device such as a plate arrangement or collimator is usually provided in the trajectory of the radiation beam between the radiation source and the object. This beam-shielding device defines a field on the object to which a prescribed amount of radiation is to be delivered.

The radiation delivered to an object may be analyzed into primary and scattered components. The primary radiation is made up of the initial or original photons emitted from the radiation source, and the scattered radiation is the result of the photons scattered by the plate arrangement itself. The beam's radiation output in free space increases because of the increased collimator scatter, which is added to the primary beam. In other words, a point in the field is subjected not only to direct radiation, that is the primary component, but also to radiation that is scattered from the plate arrangement. The ratio of the radiation output in air with the scatterer to the radiation output without the scatterer for a reference field (for instance 10×10 cm) is commonly called the "output factor" or the collimator scatter factor. The concept and definition of the output factor are well understood in the art.

Thus, due to these scattered photons, the dose rate applied to the surface of the object changes dependent on the size of the opening in the plate arrangement, that is, on the field size. This means that the radiation emitted to the same spot, for instance in the center of the radiation beam onto the object, changes according to the size of the opening in the plate arrangement. When the plate arrangement shows only a small opening, then the accumulated dose at the same spot is less than the accumulated dose at the same spot when the opening is big.

Frequently, special filters or absorbing blocks are located in the trajectory of the radiation beam to modify its isodose distribution. A most commonly used filter is the wedge filter. This is a wedge-shaped absorbing block which causes a progressive decrease in the intensity across the beam, resulting in isodose curves that are modified relative to their normal positions. Such wedge filters are usually made of dense material, such as lead or steel, or other absorbing material.

The presence of a wedge filter decreases the output of the radiation-emitting device and this decrease must be taken into account in treatment calculations. This effect is characterized by the so-called "wedge factor", defined as the ratio of doses with and without the wedge at a point in the object along the central axis of the radiation beam. The wedge factor depends on the material, size and angle of the wedge. Wedges, and particular the wedge factor, are described in Faiz M. Khan, Ph.D, "The Physics of Radiation Therapy", Williams & Wilkins, pages 234 to 238.

The delivery of radiation by such a radiation therapy device is prescribed and approved by an oncologist. Actual operation of the radiation equipment, however, is normally done by a therapist. When the therapist administers the actual delivery of the radiation treatment as prescribed by the oncologist, the device is programmed to deliver that specific treatment. When programming the treatment, the therapist has to take into consideration the output factor and has to adjust the dose delivery based on the plate arrangement opening in order to achieve the prescribed radiation output on the surface of the object. This adjustment can be made according to known calculations, but the therapist normally has to do them manually, which can easily lead to errors. In the context of radiation therapy, a miscalculation can lead to either a dose that is too low and is ineffective, or that is too high and dangerous; a large error, for example, a misplaced decimal point, can be lethal.

U.S. Pat. No. 5,148,032 discloses a radiation treatment device in which isodose curves in the object are adjusted both by a plate arrangement, which includes at least one movable plate that is controlled during irradiation, and by varying the radiation output of the radiation beam during irradiation, so that a wide range of variations in the possible isodose curves is obtained. A wedge-shaped isodose distribution is established, for example, by moving one plate at a constant speed while simultaneously changing the radiation output of the radiation beam. In this radiation treatment device there is no physical absorbing block in the trajectory of the radiation beam, and the therapist has to take this into account.

What is needed is a method, and corresponding system, for adjusting the delivery of radiation to the object in order to make sure that the actually delivered radiation output is exactly the same as the desired radiation output, independent of the use of a wedge function.

SUMMARY OF THE INVENTION

According to the invention, radiation output delivered to an object from a radiation source is adjusted by generating a radiation beam having a variable radiation output and a substantially lossless beam path from a radiation source to the object. The beam path is delimited by moving at least one beam-shielding device such as a movable plate. An irradiated field of the object is defined. The radiation output of the beam is varied as a predetermined function of the position of the beam-shielding device, a wedge factor of the radiation output thereby varying according to a predetermined profile, in which the wedge factor is defined as the ratio between a reference radiation output along a reference axis of the beam with a predetermined physical wedge in the beam path and an actual radiation output of the beam in a substantially lossless beam path. The radiation output is varied such that the wedge factor is constant regardless of the size of the irradiated field, and is preferably equal to unity.

BRIEF DESCRIPTION OF THE DRAWINGS

FIG. 2 is a block diagram illustrating portions of a processing unit, a control unit and a beam generation system in the radiation treatment device of. FIG. 1.

FIG. 3 shows isodose curves for a conventional wedge filter built of an absorption block in the path of a radiation beam.

FIG. 4 shows isodose curves for an arrangement in which a wedge filter is realized by the movement of one plate of a plate arrangement in the path of the radiation beam and by changing the radiation output of the radiation beam.

DETAILED DESCRIPTION

The invention is described below with primary reference to a system for delivering X-ray radiation to a field of a patient, and for delimiting the field using at least one movable plate in the beam path from a radiation source. This is by way of example only. The invention may be used to adjust the delivery of any type of energy, for example, electrons (instead of X-rays), to any type of object (not just a human patient), provided the amount of energy delivered to the field can be sensed or estimated.

Figure 1:
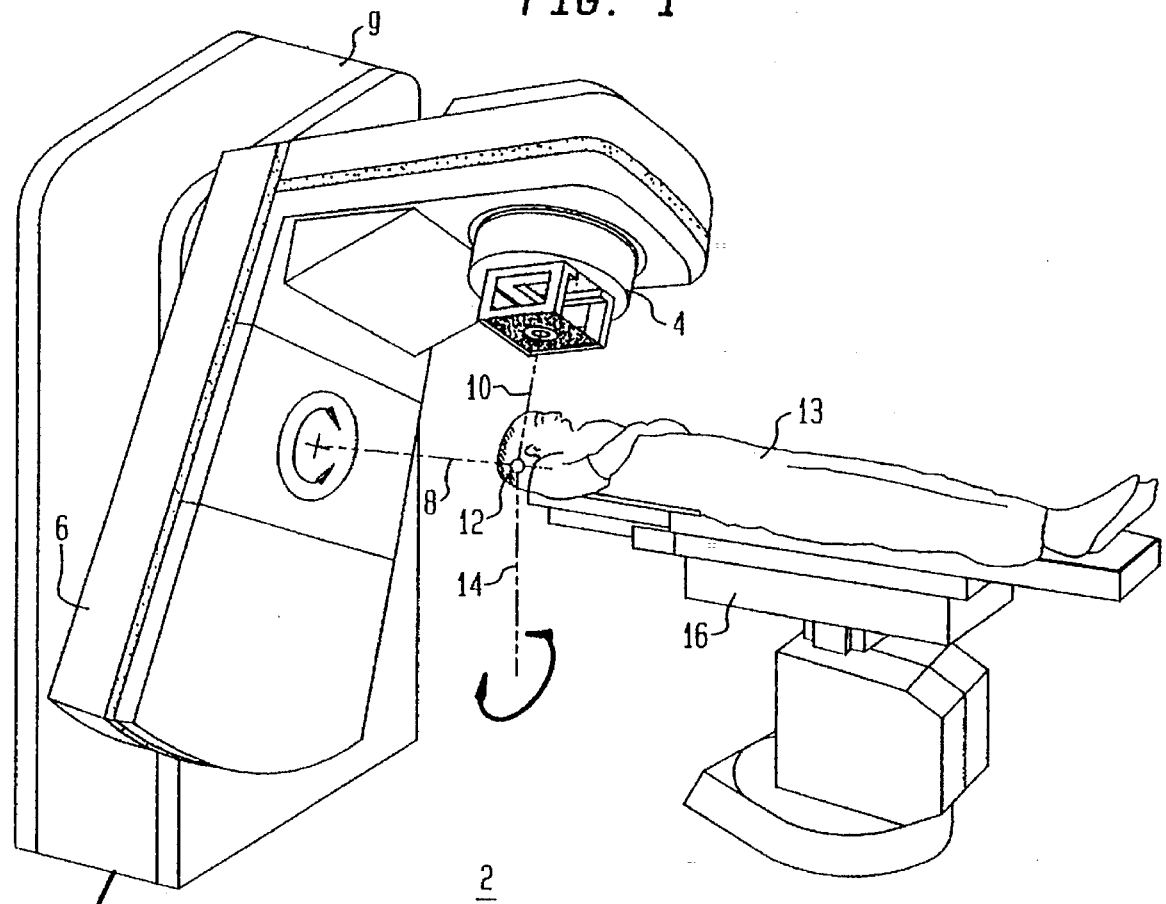
FIG. 1 shows a schematic diagram of a radiation treatment device including a treatment console constructed in accordance with the present invention.
Figure 1:
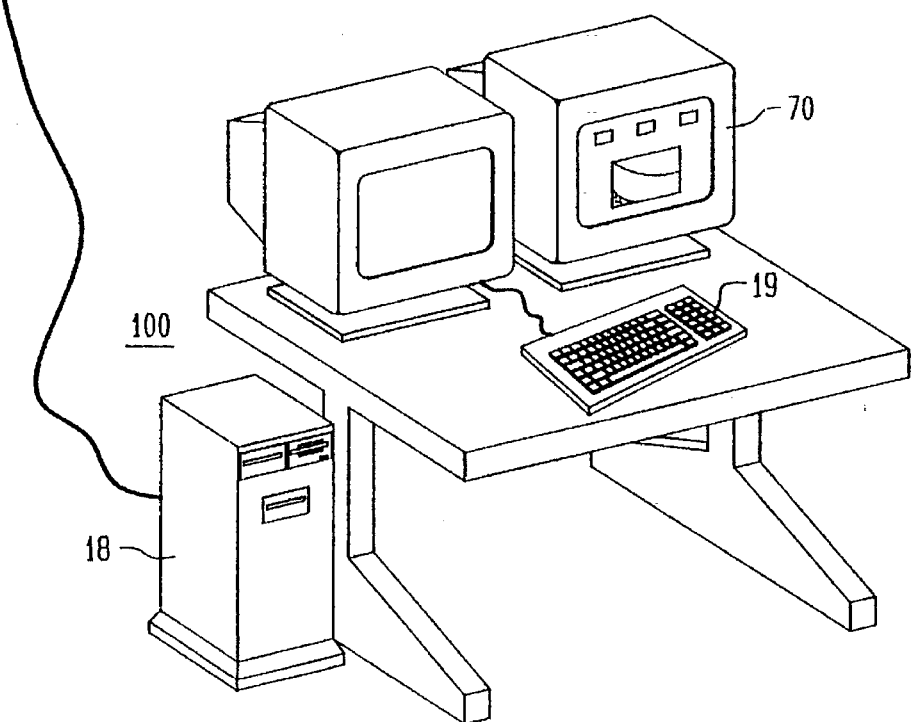

FIG. 1 shows a radiation treatment device 2 of common design, in which plates 4 and a control unit in a housing 9 and a treatment unit 100 constructed in accordance with the principles of the invention are used. The radiation treatment device 2 comprises a gantry 6 which can be swiveled around a horizontal axis of rotation 8 in the course of a therapeutic treatment. Plates 4 are fastened to a projection of gantry 6. To generate the high-powered radiation required for the therapy, a linear accelerator is located in gantry 6. The axis of the radiation bundle emitted from the linear accelerator and gantry 6 is designated by 10. Electron, photon, or any other detectable radiation can be used for the therapy.

During the treatment the radiation beam is trained on a zone 12 of an object 13, for example, a patient who is to be treated, and who lies at the isocenter of the gantry rotation. The rotational axis 8 of gantry 6, the rotational axis 14 of a treatment table 16, and the beam axis 10 all preferably intersect in the isocenter. The construction of such a radiation treatment device is described in general in a brochure "Digital Systems for Radiation Oncology", Siemens Medical Laboratories, Inc. A91004-M2630-B358-01-4A00, September 1991.

The area of the patient that is irradiated is known as the field. As is well known, the plates 4 are substantially impervious to the emitted radiation. They are mounted between the radiation source and the patient in order to delimit the field. Areas of the body, for example, healthy tissue, are therefore subjected to as little radiation as possible, and preferably to none at all. In the preferred embodiment of the invention, at least one of the plates is movable so that the distribution of radiation over the field need not be uniform (one region can be given a higher dose than another); furthermore the gantry can preferably be rotated so as to allow different beam angles and radiation distributions without having to move the patient around. Neither or these features is necessary according to the invention: the invention may also be used with fixed-field devices (no movable plates), with constant radiation delivery rates, and with fixed-angle beams (no rotatable gantry).

Radiation treatment device 2 also includes a central treatment processing or control unit 100, which is usually located apart from radiation treatment device 2. The radiation treatment device 2 is normally located in a different room to protect the therapist from radiation. Treatment unit 100 includes output devices, such as at least one visual display unit or monitor 70, and an input device such as a keyboard 19, although data can be input also through data carriers, such as data storage devices, or an verification and recording or automatic set-up system 102, which is described below. The treatment processing unit 100 is typically operated by the therapist who administers actual delivery of a radiation treatment as prescribed by an oncologist. By utilizing the keyboard 19, or other input device, the therapist enters into a control unit 76 of the treatment unit 100 the data that defines the radiation to be delivered to the patient, for example, according to the prescription of the oncologist. The program can also be input via another input device like a data storage device, through data transmission, or using the automatic set-up system 102. On the screen of a monitor 70 various data can be displayed before and during the treatment.

Figure 2:
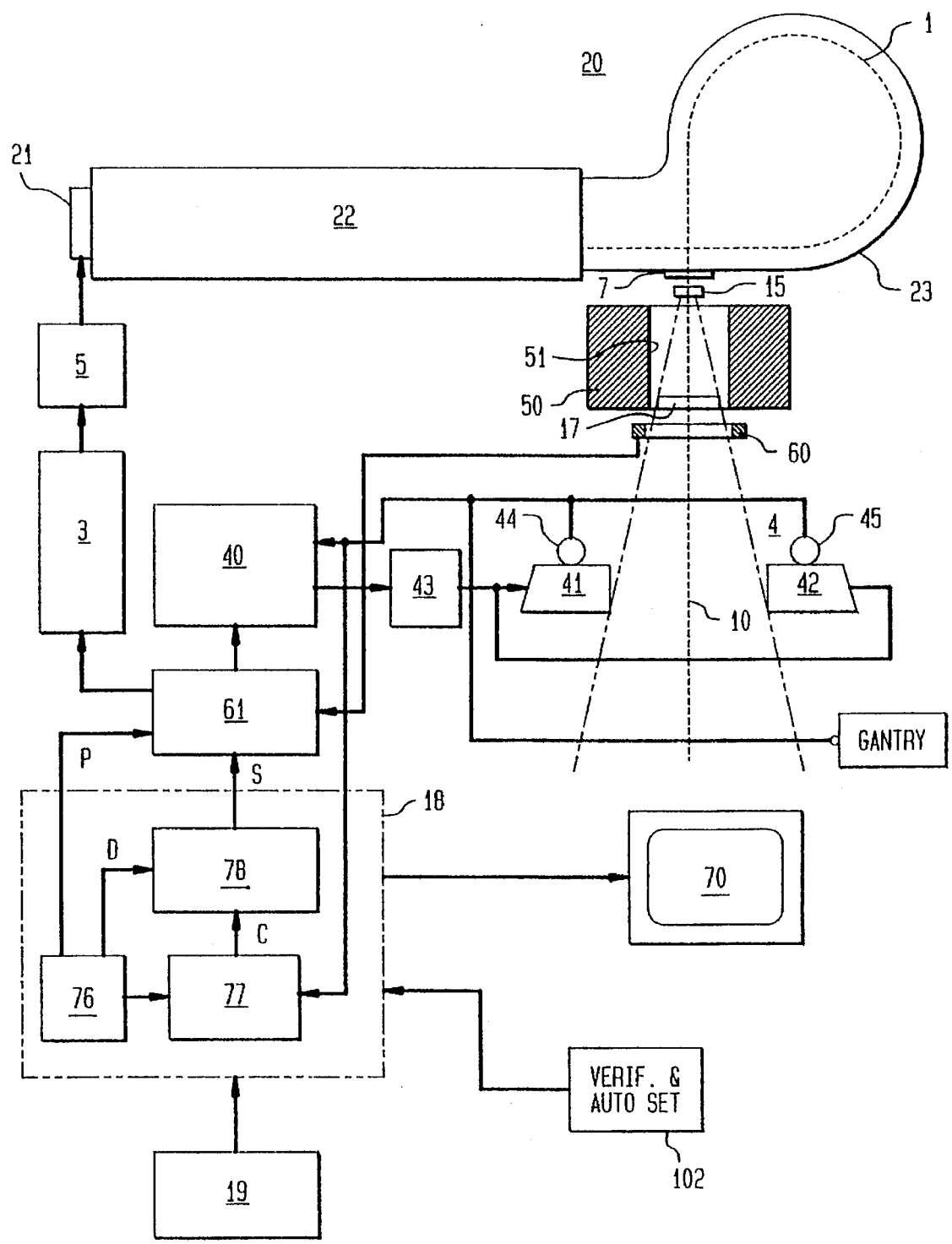

FIG. 2 shows portions of an illustrative radiation treatment device 2 and portions of treatment unit 100 in more detail. An electron beam 1 is generated in an electron accelerator 20. Accelerator 20 comprises an electron gun 21, a wave guide 22 and an evacuated envelope or guide magnet 23. A trigger system 3 generates injector trigger signals and supplies them to injector 5. Based on these injector trigger signals, injector 5 generates injector pulses which are fed to electron gun 21 in accelerator 20 for generating electron beam 1. Electron beam 1 is accelerated and guided by wave guide 22. For this purpose, a high frequency (HF) source (not shown) is provided which supplies radio frequency (RF) signals for the generation of an electromagnetic field supplied to wave guide 22. The electrons injected by injector 5 and emitted by electron gun 21 are accelerated by this electromagnetic field in wave guide 22 and exit at the end opposite to electron gun 21 as electron beam 1. Electron beam 1 then enters a guide magnet 23, and from there is guided through a window 7 along axis 10. After passing through a first scattering foil 15, the beam goes through a passageway 51 of a shield block 50 and encounters a second scattering foil 17. Next, it is sent through a measuring chamber 60, in which the dose is ascertained. If the scattering foils are replaced by a target, the radiation beam is an X-ray beam. Finally, the aperture plate arrangement 4 is provided in the path of radiation beam 1, by which the irradiated field of the subject of investigation is determined. Aperture plate arrangement 4 includes a pair of plates 41 and 42. As is described above, this is just one example of a beam-shielding arrangement that can be used in the invention. The invention will work with others also as long as there is an aperture plate arrangement that defines an irradiated field.

Plate arrangement 4 comprises a pair of aperture plates 41 and 42 and an additional pair of aperture plates (not shown) arranged perpendicular to plates 41 and 42. In order to change the size of the irradiated field the aperture plate can be moved with respect to axis 10 by a drive unit 43 which is indicated in FIG. 2 only with respect to plate 41. Drive unit 43 comprises an electric motor which is coupled to plates 41 and 42 and which is controlled by a motor controller 40. Position sensors 44 and 45 are also coupled to plates 41 and 42, respectively, for sensing their positions. This is just one example of such a system. The invention will work with other systems also, as long as them is a beam-shielding arrangement that defines an irradiated field and as long as sensors are provided to indicate the field size.

Motor controller 40 is coupled to a dose control unit 61 which includes a dosimetry controller and which is coupled to a central processing unit 18 for providing set values for the radiation beam for achieving given isodose curves. The output of the radiation beam is measured by a measuring chamber 60. In response to the deviation between the set values and the actual values, dose control unit 61 supplies signals to trigger system 3, which changes in a known manner the pulse repetition frequency so that the deviation between the set values and the actual values of the radiation beam output is minimized.

In such a radiation treatment device the dose absorbed by object 13 is dependent on the type of filter used for shaping the radiation beam. If a wedge filter built from absorbing material is inserted in the trajectory of the radiation beam, then the preset dose has to be increased according to the wedge factor in order to supply the desired dose to object 13.

FIG. 3 shows isodose curves for a conventional wedge filter 46 in the path of the radiation beam emitted from radiation source 17 to object 13. The radiation beam is shaped on the one hand by the wedge filter and on the other hand by aperture plates 41 and 42. Due to the absorbing material of wedge filter 46, the isodose curve in the center 10 of the beam on object 13 has a maximum value of Dmax, which is the maximum value at a spot in center 10 of the beam on the surface of object 13 without wedge filter 46. In the illustrated example, Dmax is roughly 72%. The wedge factor defined as the ratio of doses with and without wedge filter 46 is thus, in this case 0.72.

FIG. 4 shows isodose curves in a radiation treatment device according to the invention. Instead of including a wedge-shaped absorber in the path of the radiation beam, the filter function is performed by changing the radiation output of the radiation beam and by simultaneously moving at least one plate 41 and keeping the other plates of plate arrangement 4 stationary. A radiation treatment device having such a filter arrangement is disclosed in U.S. Pat. No. 5,148,032. Although this U.S. Patent describes the possibility of moving any plate, in the following, the invention is described in connection with only one plate being moved and the other plates being kept stationary. This is for the sake of simplicity only. The invention may be used for multiple moving plates as well.

When in FIG. 4 plate 41 moves in the direction of arrow A toward plate 42 and at the same time the radiation output is changed according to a desired wedge angle, by adjusting the speed of plate 41 and/or correspondingly, the value of the isodose curve through the center of the beam on the surface of object 13 equals Dmax=100%. Thus, by using a wedge function instead of a wedge-shaped absorber an efficiency factor of "1" or 100% can be established; in other words, the dose delivered at that point is 100% of the prescribed dose, although the same relative isodose profiles are maintained. That means that the therapist does not have to take into account a wedge factor when defining the treatment, although wedge shaped isodose curves are established.

FIG. 2 shows those portions of treatment unit 100 which are necessary to carry out the invention. Treatment unit 100 comprises central processing unit 18 and which is programmed by the therapist according to the instructions of the oncologist so that the radiation treatment device carries out the prescribed radiation treatment. Through keyboard 19 the prescribed delivery of the radiation treatment is input.

Central processing unit 18 is connected, on the one hand, with the input device, such as the keyboard 19, for inputting the prescribed delivery of the radiation treatment and, on the other hand, with a dose control unit 61 that generates the desired values of radiation for the controlling trigger system 3. Trigger system 3 then adapts the pulse repetition frequency or other parameters in a corresponding, conventional manner. The ability to change the radiation output is generally known and it is particularly advantageous to use a digital dosimetry system became then it can easily be controlled by the digital output of central processing unit 18.

Central processing unit 18 includes control unit 76 which controls the execution of the program and which supplies position signals P for controlling the opening of plate arrangement 4 and nominal dose signals D (corresponding to the plate position that would be demanded using prior art methods, that is, without regard to output factor compensation) for adjusting the radiation output at the output of radiation source 17. A memory 77 is also provided in or is connected to the central processing unit 18 for supplying correction signals C, which the processing unit uses to adjust the radiation output dependent on the position signals P supplied from position sensors 44 and 45 in order to achieve the predetermined constant output factor.

The preferred arrangement of the memory unit is that, for each plate position (field size), it has stored a corresponding wedge correction signal C. The memory thus stores a table of wedge correction factors. If more than one set of movable plates is included in the system, then the table will be correspondingly multi-dimensional, and arranged using any known data structure, so that a wedge correction factor is available for any combination of plate positions.

Control unit 76 and memory 77 apply the nominal dose and wedge correction signals D and C, respectively, to a combination circuit 78, which combines the values to generate set signals S. The set signals S are in turn applied to the dose control unit 61, which sets the radiation output.

The combination circuit 78 will depend on the form in which the wedge correction signals are generated and stored. Assume that the wedge correction signals C are stored as additive offsets to the set radiation output. In this case, the combination circuit will be an adder which adds the wedge correction signals C to nominal dose signals D. This is the preferred embodiment, since it is simplest. If, however, the wedge correction factors are multipliers, for example, an increase in radiation output from a sensed value of 72% would require a multiplicative correction signal of about 139%. Instead of storing actual values of the wedge correction signals C, it is also possible to store the parameters of a wedge correction function for the various field sizes. The processing unit would then evaluate the wedge correction function for each current field size using the parameters stored in the memory, and would then generate the wedge correction signals (additive or multiplicative) itself.

The wedge correction signals are determined before actual treatment of a patient in one or more calibration runs. To determine relative wedge correction values, a reference surface is irradiated with a known reference plate position, and the radiation output over the surface is sensed by a conventional sensing device (not shown), which generates radiation output signals, which are applied to the processing unit 18. In particular, the radiation output at a reference point (for example, at the center of the beam) is sensed. The reference surface need not lie in the patient plane, although if it does the calibration will typically be easier and more accurate.

The plates are then moved to a new opening position, the radiation output is sensed and the needed amount of adjustment is determined to create the proper isodose profile for that position. This process is continued until correction values are stored for the reference surface over the entire range of motion of the plates. If more than one set of movable plates is included, then correction values will be sensed and stored for each combination of plate positions; the number of combinations will depend on the desired or required resolution.

The correction values indicate by how much the radiation output (for example, dose rate) is to be changed (via the wedge correction signals) such that the delivered dose distribution is equal to the desired dose distribution, that is, the isodose profiles are generated corresponding to what they would be if the radiation output were held constant and a physical wedge were included in the beam path. During actual treatment, for each plate position, the processing unit adjusts the radiation output to correspond to what is needed to generate the correct isodose profile. Since no actual physical wedge is included, however, and the system is calibrated for 100% output at the reference point, the therapist need not perform any calculations to adjust for a wedge factor. If additive offsets are chosen for the wedge correction factors, then the difference between the sensed output values and the desired output value is stored. If multiplicative correction factors are chosen, then ratios are stored. Alternatively, any known function approximation method may be used to generate the parameters of an approximating function of the additive or multiplicative wedge correction factors required.

A "course" of radiation treatment may, and often does, have more than one field, and may run over several different sessions. In some cases, hundreds of different (and, in some cases, fixed) sequential fields with different wedges are used during a course, for example, to provide proper irradiation of a field that has a complicated geometry or prescribed dose profile, to lessen discomfort to the patient, or to adjust the field as a tumor shrinks during treatment. The invention therefore also comprises an optional verification and recording or "auto set-up" system 102 (see FIG. 2), which stores and downloads to the radiation system (via the CPU 18 or directly into the memory) the parameters, for example, of the geometry, of the various fields of the course of treatment, and/or the tables of wedge correction factors that were derived during earlier calibration runs for the various fields.

I claim:

1. A method for adjusting radiation output delivered to an object from a radiation source, the method comprising the steps of:

generating a radiation beam having a variable radiation output from a radiation source to the object;

delimiting the beam path by moving at least one beam-shielding device;

defining a field on the object for irradiation;

calculating a wedge correction signal, the wedge correction signal indicating how to change the variable radiation output to a desired dose distribution for the area on the object, the desired dose distribution having a wedge factor; and varying the radiation output of the radiation beam with the beam-shielding device, the varying being directly related to the wedge correction signal such that the wedge factor for the radiation output is constant regardless of the size of the irradiated field.

2. The method for adjusting radiation output delivered to an object from a radiation source of claim 1, wherein the wedge correction signal is an additive offset.

3. The method for adjusting radiation output delivered to an object from a radiation source of claim 2, wherein a circuit adds the wedge correction signal to at least one nominal dose signal.

4. The method for adjusting radiation output delivered to an object from a radiation source of claim 1, wherein the wedge correction signal is stored in a memory, and wherein a program uses the stored wedge correction signal to vary the radiation output of the radiation beam.

5. The method for adjusting radiation output delivered to an object from a radiation source of claim 1, wherein the wedge correction signal is a wedge correction factor.

6. The method for adjusting radiation output delivered to an object from a radiation source of claim 5, wherein the wedge correction factor is a multiplier.

7. The method for adjusting radiation output delivered to an object from a radiation source of claim 5, wherein parameters of the wedge correction factor are stored for various field sizes.

8. The method for adjusting radiation output delivered to an object from a radiation source of claim 5, wherein the wedge correction factor is associated with at least one of the beam-shielding devices.

9. A system for adjusting radiation output delivered to an object from a radiation source, comprising:

a radiation source generating a radiation beam having a variable radiation output;

identifying means for defining a field on the object for irradiation;

beam shielding means for delimiting the variable radiation output from the radiation beam to at least one defined irradiation field on the object;

a dose controller for varying a degree of shielding of the radiation beam such that a desired dose distribution is obtained the desired dose distribution having a wedge factor; and means for calculating a correction signal, and for using the correction signal for varying the radiation output such that the wedge factor is constant regardless of the size of the irradiation field.

10. The system for adjusting radiation output delivered to an object from a radiation source of claim 9, wherein the correction signal is obtained from a plurality of additive offsets.

11. The system for adjusting radiation output delivered to an object from a radiation source of claim 9, wherein the correction signal is obtained from plurality of multipliers.

* * * * *